United States Patent [19]
Wielsch et al.

[11] Patent Number: 5,526,117
[45] Date of Patent: Jun. 11, 1996

[54] METHOD FOR THE DETERMINATION OF CHARACTERISTIC VALUES OF TRANSPARENT LAYERS WITH THE AID OF ELLIPSOMETRY

[75] Inventors: Uwe Wielsch; Uwe Richter, both of Berlin; Helmut Witek, Planegg; Albrecht Krüger, Berlin, all of Germany

[73] Assignee: Sentech Instruments GmbH, Berlin, Germany

[21] Appl. No.: 181,950

[22] Filed: Jan. 14, 1994

[30]   Foreign Application Priority Data

Jan. 14, 1993 [DE]   Germany .......................... 43 01 889.0

[51] Int. Cl.$^6$ ................................................. G01N 21/21
[52] U.S. Cl. .......................... 356/369; 356/382; 356/128; 356/322
[58] Field of Search .................................... 356/364, 365, 356/366, 367, 368, 369, 381, 382, 128, 319, 320, 322, 326, 327; 250/225

[56]   References Cited

U.S. PATENT DOCUMENTS 4,790,659   12/1988   Erman et al. ........................... 356/369

FOREIGN PATENT DOCUMENTS 3779568   10/1987   Germany .
3926184.0   8/1989   Germany .
4108329.6   3/1991   Germany .

OTHER PUBLICATIONS

Neal, W. E. J. et al., "Ellipsometry and its applications to surface examination" *Journal of Physics E: Scientific Instruments 1973*, vol. 6, p. 409.

Thompkins, H. G. "A User's Guide to Ellipsometry" pp. 40–45.

*Primary Examiner*—Hoa Q. Pham
*Attorney, Agent, or Firm*—Christie, Parker & Hale

[57]   ABSTRACT

Characteristic values of transparent layers in the nanometer range, such a layer thickness and refractive index, can be determined with a spectro-ellipsometer. The task is to determine these values even with a less elaborate ellipsometer which only operates at one or a few wavelengths. In accordance with the invention, first at least one pair of the ellipsometric angles psi and delta are measured with at least one angle of incidence of the light beams on the sample for at least one ellipsometer wavelength, from which at least one characteristic value is determined for one ellipsometer period. Furthermore, the wavelength-dependent reflection of the probe in the wavelength range of interest is photometrically measured and from this the spectral dependency of the characteristic value is determined with the ellipsometrically measured characteristic value.

11 Claims, 2 Drawing Sheets

METHOD FOR THE DETERMINATION OF CHARACTERISTIC VALUES OF TRANSPARENT LAYERS WITH THE AID OF ELLIPSOMETRY

FIELD OF THE INVENTION

The invention relates to the ellipsometric determination of transparent thin layers in the nanometer range, in particular for use in optics and in semiconductor technology.

BACKGROUND OF THE INVENTION

With known ellipsometers, a sample is exposed to radiation by a linear-polarized laser beam, for which purpose a laser with a polarizer and a compensator is arranged. The laser beam impinges obliquely on the sample, is reflected on its surface and is directed in the form of an elliptically polarized beam to a photo detector via a rotating analyzer. As a rule, the output signals of the photo detector are supplied to a computer for evaluation of the measuring signals. In ellipsometry, the change of the polarization state of the reflected light is measured. The reflection ratio between parallel and vertically polarized light is a function of the layer thickness, among others (DE-OS 39 26 184, DE-OS 41 08 329, the disclosure of which is expressly incorporated herein by reference).

The advantage of ellipsometry as compared to, for example, photometry consists in that the independent measurement of two parameters, for example thickness and refractive index, is possible in one measuring operation. Furthermore, a rapid measurement of high accuracy is possible.

The disadvantage of simple ellipsometers operating with one wavelength lies in that no spectral information is obtained and that measurement of the layer thickness is only possible within one ellipsometric period. If there is no statement regarding the period, it is also not possible to make a statement regarding the absolute layer thickness.

A further disadvantage lies in that high measuring accuracy depends on the film thickness if the refractive index is unknown. The interrelationship is shown in FIG. 1. The ellipsometric angles psi and delta for different refractive indices are shown there. In the area of the focus, which is located at a delta value of 180°, i.e. when measuring layers of a thickness of approximately 220 to 340 nanometers, an independent measurement of the layer thickness and of the refractive index is not possible.

Spectral photometers (DE-OS 39 26 184) are also known for measuring the thickness of transparent layers. With these, the layer to be tested is illuminated with white light, i.e. with light having a sufficiently large range of wavelengths. If such radiation is reflected by a transparent layer, the portions reflected at the front and the rear boundary surface travel over different distances.

When they are superimposed, interferences are created, i.e. the reflected radiation is either increased or decreased or cancelled as a function of the optical layer thickness and wavelength. The reflectivity is a function of the product of refractive index times layer thickness, so that it is possible to detect the layer thickness if the refractive index is known.

Measuring with the spectral photometer has the disadvantage that the simultaneous determination of the layer thickness as well as of the refractive index is not possible in one measurement because of the spectral dependence on the refractive index.

The mentioned disadvantages can be avoided by using a spectro-ellipsometer. With this, the measurements are performed in a continuously variable spectrum.

However, the disadvantage of the spectro-ellipsometer lies in that its construction is very elaborate and thus expensive.

It is the object of the invention to determine, in the course of ellipsometric measurements of transparent films on reflecting substrates at one wavelength or with a few discrete wavelength, at least two characteristic values of the film, such as layer thickness and refractive index and the dispersion, with great precision, even with layer thicknesses wherein at least one of the characteristic values at one wavelength or a few discrete wavelengths could not or could only be inaccurately detected up to now, and in addition to determine the spectral dependence of the characteristic values.

SUMMARY OF THE INVENTION

In accordance with the invention there is provided a method for the determination of characteristic values of transparent layers with the aid of ellipsometry, characterized in that first at least one pair of the ellipsometric angles psi and delta are measured with at least one angle of incidence of the light beams on the sample for at least one ellipsometer wavelength, from which by means of relationships known per se at least one characteristic value of the transparent film to be measured is determined for one ellipsometer period, that in a second step, the wavelength-dependent reflection of the sample in the wavelength range of interest is photometrically measured and from this the spectral dependency of the characteristic values is determined as a starting value by means of a known relationship and with the aid of a characteristic value of the transparent film determined in the first step at the discrete ellipsometric wavelength(s).

DETAILED DESCRIPTION

Figure 1:
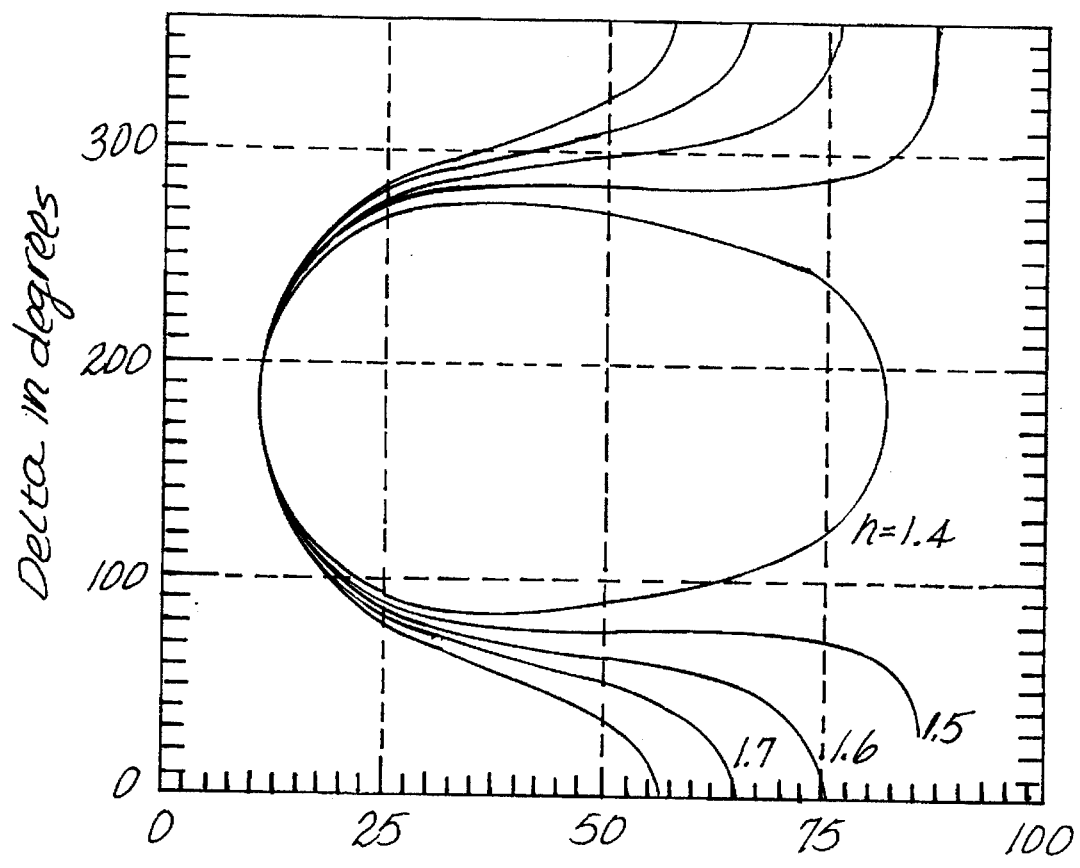
FIG. 1 is a graph showing the relationship between the delta and psi of ellipsometric angles at different refractive indices.

With the method of the invention, first at least one pair of the ellipsometric angles psi and delta are measured with at least one angle of incidence of the light beams on the sample for at least one ellipsometer wavelength, from which by means of relationships known per se, at least one characteristic value of the transparent film to be measured is determined for one ellipsometer period. In a second step, the wavelength-dependent reflection of the sample in the wavelength range of interest is photometrically measured and from this the spectral dependency of the characteristic values is determined as a starting value by means of a known relationship and with the aid of a characteristic value of the transparent film determined in the first step at the discrete ellipsometric wavelength(s).

In the first step it is possible to determine, as the characteristic value, the layer thickness d and the refractive index n of the film to be measured for one ellipsometer period, wherein the ellipsometric order is at first unknown. Subsequently, with the help of the wavelength-dependent reflection of the sample determined in the second step, the absolute layer thickness is determined by approximation by means of a known relationship with the assumption of the constant refractive index determined in the first step. In a further step, the accuracy of the layer thickness determined in the second step is improved with the help of a known relationship by means of the absolute layer thickness determined in the second step and with the aid of the layer thickness determined in the first step. Having this layer thickness and the ellipsometrically determined refractive index as starting values, the spectral dependency of the refractive index is finally determined through a known relationship.

For the case where the ellipsometer angle delta lies in the range of 180° and where it is therefore only possible to exactly determine the product of the refractive index and the layer thickness n×d from the measured ellipsometer angles psi and delta, but where the individual values n and d can only be inaccurately determined, in accordance with the invention the refractive index n and the layer thickness d are determined in a first step, with the large inaccuracies which are a condition of the method. In a second step, the wave-dependent reflection is measured spectro-photometrically. In a third step, a more accurate value of the layer thickness is determined with this measured reflection value and the ellipsometrically determined refractive index in accordance with a known relationship. With this newly determined layer thickness and the ellipsometrically determined refractive index an improved value of the refractive index is determined in a fourth step. In a fifth step an improved value of the layer thickness is determined by means of this improved value of the refractive index. The method steps recited in the fourth and fifth steps are iteratively continued until the values for the layer thickness and the refractive index remain constant and thus both values have been determined with ellipsometric accuracy.

The known relationship between the refractive index and the remaining values is:

$$n = n_c + a(w^2 - w_e^2) + b(w^4 - w_e^4)$$

$$n_c = n_0 + a\, w_e^2 + b\, w_e^4$$

wherein n is the refractive index of the film $n_c$ is the refractive index which was ellipsometrically determined at one wavelength $n_0$, a, b are dispersion coefficients w is the wave number $w_e$ the ellipsometer wave number at which measuring takes place.

The interrelationships will be described by means of diagrams. Shown are in

Figure 2:
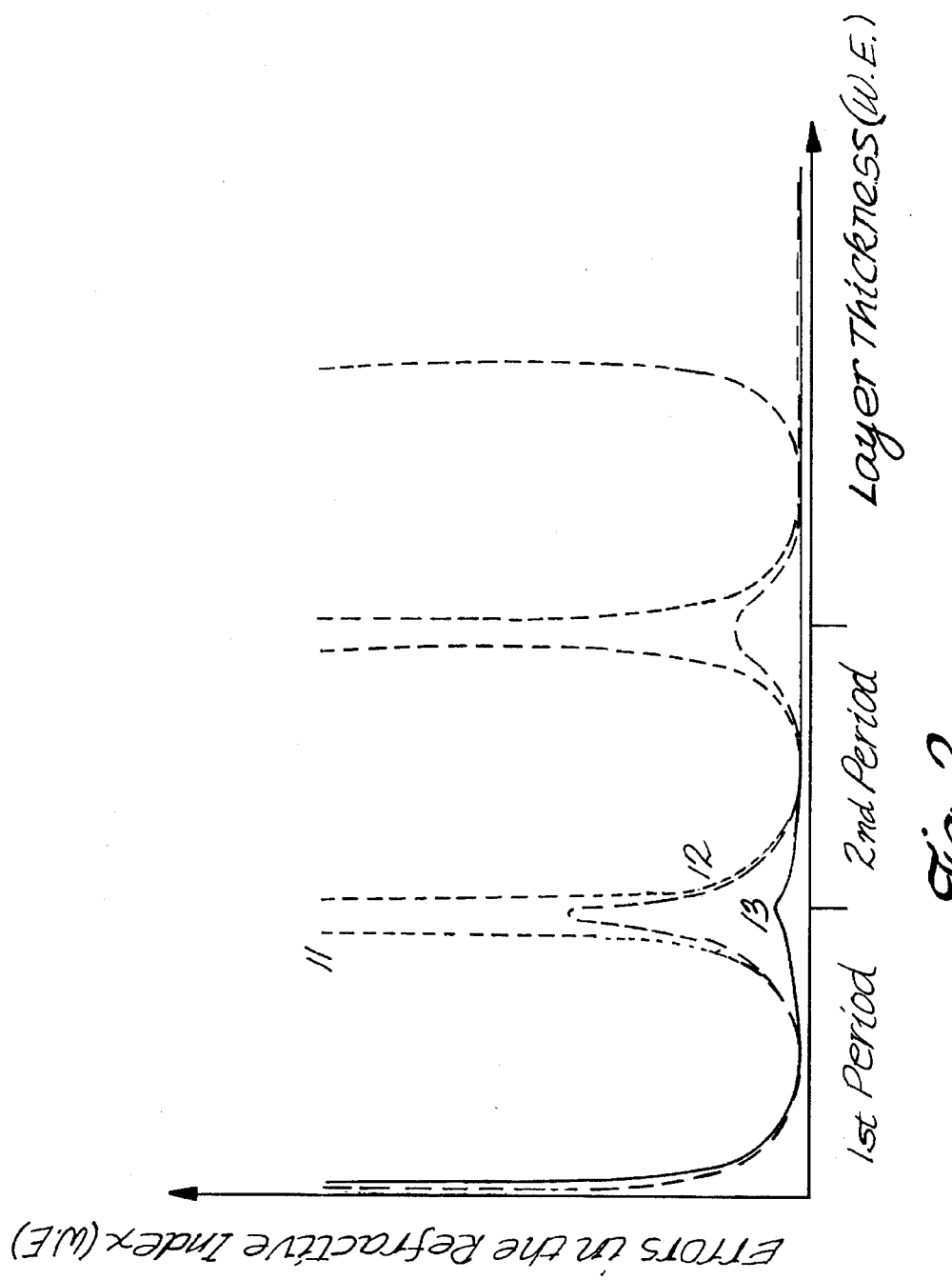
FIG. 2 is a graph showing a curve that illustrates the error in refractive index for different ellipsometric angles.

FIG. 1, the illustration of the ellipsometric angles psi and delta at different refractive indices FIG. 2, the curve of the error in the refractive index for different ellipsometric angles.

The dependency of the layer thickness from the accuracy of the measurement of the refractive index n can be seen in FIG. 2. It can be seen that at half-periods and periods, i.e. when the ellipsometric angle is 180° or a whole number multiple thereof, the refractive index can only be determined very inaccurately. This disadvantage is removed by the method of the invention. With a single angle measurement, the curve 11 of the error results which has the mentioned large errors at the half-periods and periods. With the multiple angle measurement the error is reduced to the curve 12.

The error curve 13 is achieved with the method of the invention and thus a minimization of errors at the half-periods and periods.

In a special embodiment of the method, at an ellipsometer angle delta of 180°, the error curve 11 can be improved to an error curve 13.

The disclosure of attached German patent application P 43 01 889.0, filed on Jan. 14, 1993, is incorporated fully herein by reference. Priority of this German application is claimed.

What is claimed is:

1. A method for determining characteristic values of a transparent layer by ellipsometry comprising:

providing a sample having a transparent layer thereon;

measuring at least one pair of ellipsometric angles psi and delta with at least one angle of incidence of a light beam on the sample for at least one ellipsometric wavelength;

determining a first thickness value of the layer on the sample and a first refractive index value for one ellipsometric period; and spectro-photometrically measuring a wavelength-dependent reflection at said ellipsometric wavelength, wherein a second layer thickness value is determined from the wavelength-dependent reflection of the sample and from the first refractive index value.

2. A method according to claim 1 further comprising ellipsometrically determining a second refractive index value from the second layer thickness value measurement and the ellipsometrically determined first refractive index value.

3. A method according to claim 2 wherein successive thickness and refractive index values are ellipsometrically determined iteratively until the value of the layer thickness and refractive index remain constant.

4. A method for determining characteristic values of a transparent film layer comprising the steps of:

providing a sample having said transparent film layer thereon;

measuring at least one pair of ellipsometric angles psi and delta with at least one angle of incidence of a light beam on the sample at at least one ellipsometer wavelength such that at least one characteristic value of the transparent film layer is determined for one ellipsometer period;

spectro-photometrically measuring a wavelength-dependent reflection of a sample at a predetermined wavelength; and calculating from said wavelength-dependent reflection a spectral dependency of said characteristic values based on said at least one characteristic value of the transparent film layer determined for said one ellipsometer period at said one ellipsometer wavelength.

5. A method according to claim 4 wherein said characteristic values of the transparent film layer comprise the layer thickness and the refractive index, the at least one characteristic value of the transparent film layer determined for one ellipsometric period at at least one ellipsometric wavelength comprises the refractive index.

6. A method according to claim 5 wherein a true layer thickness value is determined from the wavelength dependent reflection of the sample and from the refractive index value.

7. A method according to claim 5 wherein the spectral dependency is the spectral dependency of the refractive index.

8. A method according to claim 7 wherein the spectral dependency of the refractive index is determined from the true layer thickness and the ellipsometrically determined refractive index.

9. A method for ellipsometrically determining characteristic values of transparent layers comprising the steps of:

providing a sample having a transparent layer thereon;

measuring at least one pair of ellipsometric angles psi and delta with at least one angle of incidence of a light beam on the sample at a single, discrete, ellipsometric wavelength;

determining a first thickness value of the layer on the sample and a first refractive index value for one ellipsometric period;

spectro-photometrically measuring a wavelength-dependent reflection at a predetermined wavelength; and determining a second layer thickness value from the wavelength-dependent reflection of the sample and the first refractive index value.

10. A method according to claim 9 further comprising ellipsometrically determining a second refractive index value from the second layer thickness value.

11. A method according to claim 10 wherein successive thickness and refractive index values are ellipsometrically determined iteratively until the value of the layer thickness and refractive index remain constant.

\* \* \* \* \*